United States Patent [19]

Frey

[11] 4,003,096
[45] Jan. 18, 1977

[54] WRIST JOINT ENDOPROSTHESIS

[75] Inventor: Otto Frey, Winterthur, Switzerland

[73] Assignee: Sulzer Brothers Limited, Winterthur, Switzerland

[22] Filed: May 24, 1976

[21] Appl. No.: 688,995

[30] Foreign Application Priority Data

June 17, 1975 Switzerland .................. 7807/75

[52] U.S. Cl. .................. 3/1.91; 128/92 C
[51] Int. Cl.² .................. A61F 1/24
[58] Field of Search .................. 3/1, 1.9–1.913, 3/12.4; 128/92 C, 92 CA

[56] References Cited

UNITED STATES PATENTS

| 3,506,982 | 4/1970 | Steffee | 3/1.91 |
| 3,708,805 | 1/1973 | Scales et al. | 3/1.91 |
| 3,837,008 | 9/1974 | Bahler et al. | 3/1.91 |
| 3,886,601 | 6/1975 | Findlay | 3/1 |
| 3,899,796 | 8/1975 | Bahler et al. | 3/1.91 |

FOREIGN PATENTS OR APPLICATIONS

| 2,309,432 | 11/1973 | Germany | 3/1.91 |

*Primary Examiner*—Ronald L. Frinks
*Attorney, Agent, or Firm*—Kenyon & Kenyon Reilly Carr & Chapin

[57] ABSTRACT

An intermediate member is positioned between the proximal joint part and the distal joint part in order to permit increased hand movements. The intermediate member has a V-shaped recess which receives an extension of the proximal joint part and allows an extra degree of movement. The distal joint part has a spherical joint head which is snapped into a socket in the intermediate member.

6 Claims, 7 Drawing Figures

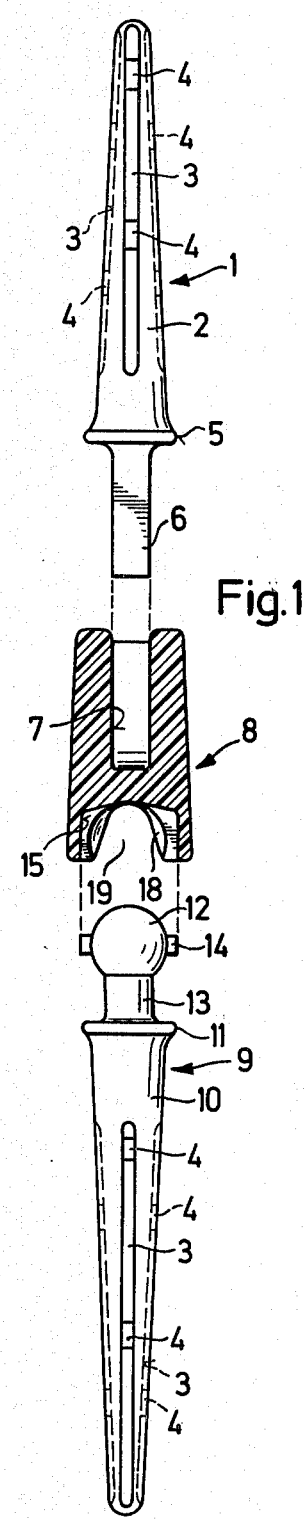
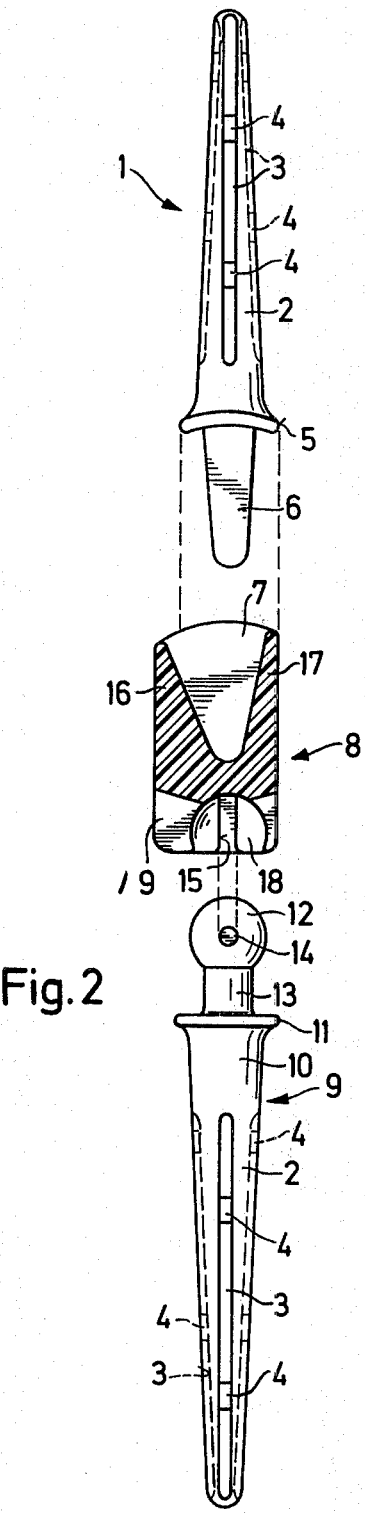

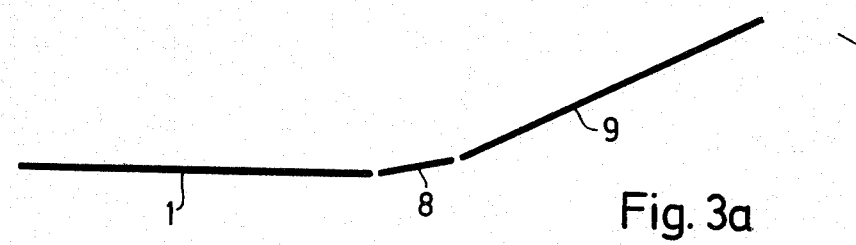
Fig. 3a
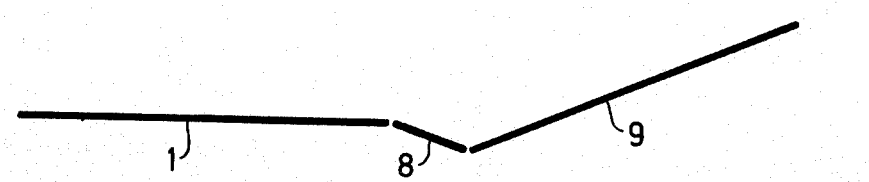
Fig. 3b
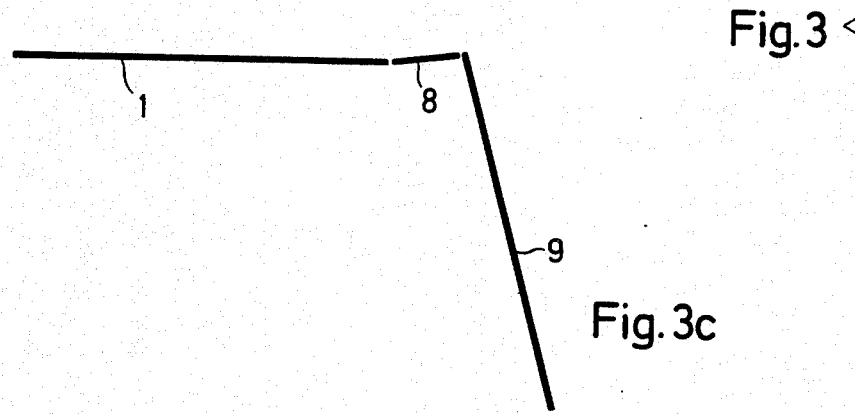
Fig. 3c
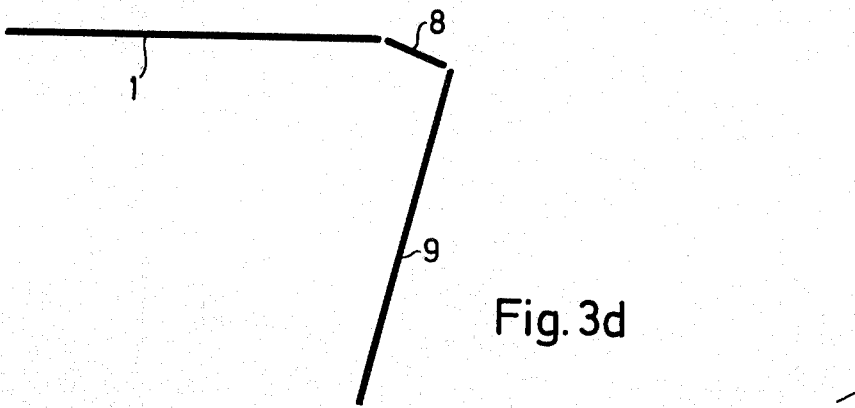
Fig. 3d
Fig. 3

WRIST JOINT ENDOPROSTHESIS

This invention relates to a wrist joint endoprosthesis.

As is known, wrist joint prostheses are usually constructed of components which are interconnected by a socket-type joint. In such cases, the endoprosthesis includes a spherical joint head on one component which is adapted to be pushed through a jaws-like aperture into a spherical socket as well as at least one extension which engages in a corresponding slotlike recess of the socket to secure the joint head against rotation around an axis extending in the direction of the intramedullary stem. However, it has been found in practice that known endoprostheses of this kind (Swiss Patent Specification 541,962) provide only limited and unsatisfactory hand movements since mobility of the axis is concentrated just at one place of the joint, viz. movement of the spherical joint head in the socket.

Accordingly, it is an object of this invention to improve the mobility of wrist joint endoprostheses.

It is another object of the invention to adapt a wrist joint prosthesis more closely to the motions of a natural wrist joint.

Briefly, the invention provides a wrist joint prosthesis which is composed of a proximal joint part adapted for anchoring in a forearm, a distal joint part adapted for anchoring in at least one metacarpal bone and an intermediate member between the joint parts.

The proximal joint part includes an extension at a distal end which is formed with a pair of parallel side walls.

The distal joint part has an intramedullary stem disposed on a longitudinal axis at one end, a spherical joint head at an opposite end and at least one extension projecting from the spherical joint head.

The intermediate member has a spherical socket at one end which receives the spherical joint head, a jaw-like aperture which opens into the socket and through which the joint head passes and at least one groove in the socket which receives the extension of the joint head in order to prevent rotation of the joint head about an axis extending in the direction of the intramedullary stem. The intermediate member also has a slotlike recess at the opposite end which receives the extension of the proximal joint part. This recess is of V-shape in a plane perpendicular to the socket groove and has at least substantially parallel side walls in the plane of the socket groove.

The extension on the proximal joint part is, at most, of V-shape in the plane perpendicular to the socket groove with a relatively flat angle of opening and has a pair of parallel side walls in the plane of the groove.

The intermediate member between the proximal and distal joint parts does not impair the existing mobility of the endoprosthesis mentioned. However, the fact that the intermediate member can pivot relative to the extension of the proximal joint part via the V-shaped recess in the intermediate member provides an extra degree of freedom of movement. Consequently, the center of the joint is capable of limited upwards and downwards movement so that a closer approximation to natural wrist joint mobility is achieved. Advantageously, the V-shaped recess can be asymmetrical of its center-plane so that a greater degree of pivoting can occur in one direction than in the opposite direction.

If the intermediate member is made of plastics, particularly high-molecular-weight hard polyethylene, any rubbing together of the two joint parts is obviated. This is advantageous especially when the joint parts are made of metal.

Also, if the intermediate members are made in different sizes, a single size or just a few sizes for the proximal and distal joint parts are all that is needed to allow the production of joints of various lengths.

Since the two joint parts are merely pushed into the intermediate member, connecting the joint parts together during the operation is greatly simplified and becomes a task which can be carried out without special tools. This known relatively readily releasable push connection also makes it possible to obviate or, at least, to reduce substantial damage or injury to the tissue, muscles and/or adjacent joints in the case of traumatic overloading of the joint.

These and other objects and advantages of the invention will become more apparent from the following detailed description and appended claims taken in conjunction with the accompanying drawings in which:

FIG. 1 illustrates an exploded view of the individual elements of a wrist joint endoprosthesis according to the invention in plan onto a hand with the joint implanted and with the intermediate member being shown in section;

FIG. 2 illustrates a similar view to FIG. 1 in side elevation; and

FIGS. 3a to 3d diagrammatically illustrate the position of the longitudinal axes of the individual elements in various end positions.

Referring to FIGS. 1 and 2, the wrist joint prosthesis is constructed of three elements including a proximal joint part 1, a distal joint part 9 and an intermediate member 8 which articulates the two joint parts 1, 9 to each other.

The proximal joint part 1 is produced preferably from a metal used in the implant art or from a metal alloy and has a shank or stem 2 which is in cross-section substantially circular and which is formed with longitudinal recesses 3 and cross-grooves 4. The stem 2 serves to anchor the joint part 1 in a radius bone (not shown) of a forearm and can be both cemented in with a known bone cement and also secured by invasion of tissue, the recesses 3 and grooves 4 helping to improve the anchoring and to prevent the stem 2 from turning. Of course, two or more e.g. pin-like anchoring elements can be provided instead of a single stem 2. The stem 2 terminates at the distal end in a plate-like shoulder 5 which serves as a stop to limit the depth to which the stem 2 can penetrate into the bone (not shown).

The proximal joint 1 also has an extension 6 at the distal end which is adapted to engage in a recess 7 in the intermediate member 8. As seen in plan, the extension 6 is a rectangular member having parallel side walls which, as seen in side elevation (FIG. 2), has a slightly conical shape symmetrically of the center-plane thereof so as to present at most a V-shape with a relatively flat angle of opening (FIG. 2). Also, the free end of the extension 6 is rounded. As FIG. 2 also shows, the surface of the plate-like shoulder 5 which is near the extension 6 is arcuate to facilitate relative movement between the joint part 1 and the intermediate member 8.

The distal joint part 9 is also preferably made of metal and has an intramedullary stem or shank or the like 10 at one end which is similar to the stem 2 and which merges into a shoulder 11 similar to the shoulder 5 on the proximal joint part 1. This stem 10 serves to anchor the joint part 9 in a metacarpal bone (not shown) and is disposed on a longitudinal axis. In addition, the distal joint part 9 has a spherical joint head 12 at the proximal end which bears by way of a cylindrical neck 13 on the shoulder 11. The head 12 has at least one extension, for example two, in the form of lugs 14 which project from the joint head 12 along the head axis which is disposed in a horizontal plane as viewed. These lugs 14 serve in known manner to engage in corresponding grooves 15 (FIG. 2) in the intermediate member 8 to prevent accidental rotation of the distal joint part 9 around a forearm axis which is assumed to be vertical in the plane of the drawing.

The intermediate member 8 into which the two joint parts 1, 9 can be pushed is preferably made of plastics such as a high-molecular-weight hard polyethylene and is therefore of the necessary resilience to permit the two metals parts 1, 9 to be pushed thereinto.

At the proximal end, the intermediate member 8 is formed with a recess 7 which is rectangular in plane. As seen in side elevation, the recess 7 widens conically upwards and downwards and is rounded at the base. The distal end of the member 8 is formed with a hollow spherical socket 18 whose center plane widens from the edge into the grooves 15 (FIG. 1). In addition, a jaw-like aperture 19 opens into the socket 18. In the assembled prosthesis, this aperture 19 receives the cylindrical neck 13 of the distal joint part 9 and provides mobility of the distal part 9 of the wrist joint in flexing and extension and in lateral movements of the wrist joint. The aperture 19 can have different angles of opening for flexing and extension, the angle for flexing permitting a greater movement.

As can be seen in FIG. 2, the conical recess 7 is asymmetric of the center-plane of the hollow spherical socket 18 which is adapted to receive the joint head 12. In addition, the recess 7 is formed with two inclined walls 16, 17 which define a V-shape in a plane perpendicular to the grooves 15 in the socket 18 and with at least substantially parallel side walls in the plane of the grooves 15. The shape of the recess 7 thus accommodates the shape of the extension 6 of the proximal joint part 1.

During assembly, the proximal joint part 1 is implanted and the intermediate member 8 is arranged so that the more open wall 16 of the member 8 extends downwards, i.e. towards the surface of the hand and the shallower wall 17 extends towards the back of the hand. Thereafter, the head 12 of the distal joint part 9 is introduced into the socket 18 by way of the jaws-like aperture 19.

As already mentioned, FIG. 3 shows in diagrammatic form possible relative settings of the various elements 1, 8, 9 of the prosthesis. FIGS. 3a and 3b are views in diagrammatic and simplified form to show the position of the elements 1, 8, 9 with the hand extended, as occurs e.g. when an article is raised with the palm facing upwards (FIG. 3a) or when the palm provides support when the trunk (upper part of the body) bears on a substantially horizontal plate (FIG. 3b). FIG. 3c shows the position of the axes of the elements 1, 8, 9 when the extended fingers are pushed down on to an at least substantially horizontal surface, while FIG. 3d shows the position of the axes in the case of a completely flexed hand on which no force is acting. Of course, a wide variety of interemdiate positions are possible between the end positions shown.

To give some idea of the quantities already achieved for the various angles in one embodiment of the invention, the extension of the distal joint part 9 relative to the proximal joint part 1 can be e.g. − 75° and the flexing can be +25°; the upwards angle is called positive and the downwards angle is called negative. There is lateral mobility of 25° in both directions.

The recess 7 in the intermediate member 8 can be disposed relative to the proximal joint part 1 to define an angle of about +8° upwards and a maximum angle of −22° downwards.

What is claimed is:

1. A wrist joint endoprosthesis comprising
    a proximal joint part adapted for anchoring in a forearm, said joint part including an extension at a distal end having a pair of parallel side walls;
    a distal joint part adapted for anchoring in at least one metacarpal bone, said distal joint part having an intramedullary stem disposed on a longitudinal axis at one end, a spherical joint head at an opposite end and at least one extension projecting from said spherical joint head; and
    an intermediate member between said joint parts, said intermediate member having a spherical socket at one end receiving said spherical joint head therein, a jaw-like aperture opening into said socket, at least one groove within said socket receiving said extension of said joint head to prevent rotation of said joint head about an axis extending in the direction of said intramedullary stem, and a slot-like recess at an opposite end of said intermediate member receiving said extension of said proximal joint part, said recess being of V-shape in a plane perpendicular to said groove in said spherical socket and having at least substantially parallel side walls in the plane of said groove.

2. A wrist joint prosthesis as set forth in claim 1 wherein said extension of said proximal joint part is at most of V-shape in said plane perpendicular to said groove in said spherical socket with a relatively flat angle of opening and has a pair of parallel side walls in the plane of said groove.

3. A wrist joint prosthesis as set forth in claim 1 wherein said V-shaped recess of said intermediate member is asymmetrical of the center plane thereof.

4. A wrist joint prosthesis as set forth in claim 1 wherein said intermediate member is made of plastics and said joint parts are each made of metal.

5. A wrist joint prosthesis as set forth in claim 4 wherein said intermediate member is made of high-molecular-weight hard polyethylene.

6. A wrist joint endoprosthesis comprising
    a proximal joint part adapted for anchoring in a forearm and including an extension having a pair of parallel side walls;
    a distal joint part adapted for anchoring in at least one metacarpal bone and including a spherical joint head having at least one extension projecting therefrom; and
    an intermediate member between said joint parts having a spherical socket at one end receiving said joint head, a groove within said socket receiving said extension of said joint head to prevent rotation of said joint head about an axis longitudinal of said distal joint part, and a slot-like V-shaped recess at an opposite end receiving said extension of said proximal joint part, said recess having a pair of parallel side walls in the plane of said groove to guide said side walls of said joint extension.

* * * * *